US012128060B2

(12) United States Patent
Dellinger et al.

(10) Patent No.: US 12,128,060 B2
(45) Date of Patent: Oct. 29, 2024

(54) NICOTINAMIDE RIBOSIDE FOR USE IN TREATING OR PREVENTING LIVER DAMAGE

(71) Applicant: Elysium Health, Inc., New York, NY (US)

(72) Inventors: Ryan Dellinger, Azusa, CA (US); Santiago Roel Santos, New York, NY (US); Eric A. Marcotulli, New York, NY (US); Daniel A. Alminana, New York, NY (US); Mark Morris, New York, NY (US); Leonard Pershing Guarente, Newton, MA (US)

(73) Assignee: Elysium Health, Inc., New York, NY (US)

( * ) Notice: Subject to any disclaimer, the term of this patent is extended or adjusted under 35 U.S.C. 154(b) by 0 days.

(21) Appl. No.: 17/842,042

(22) Filed: Jun. 16, 2022

(65) Prior Publication Data
US 2022/0305040 A1    Sep. 29, 2022

Related U.S. Application Data

(62) Division of application No. 16/494,581, filed as application No. PCT/US2018/022854 on Mar. 16, 2018, now Pat. No. 11,389,468.

(60) Provisional application No. 62/472,883, filed on Mar. 17, 2017.

(51) Int. Cl.
| | |
|---|---|
| *A61K 31/706* | (2006.01) |
| *A61K 9/00* | (2006.01) |
| *A61K 31/09* | (2006.01) |
| *A61P 1/16* | (2006.01) |

(52) U.S. Cl.
CPC .......... *A61K 31/706* (2013.01); *A61K 9/0053* (2013.01); *A61K 31/09* (2013.01); *A61P 1/16* (2018.01)

(58) Field of Classification Search
CPC ....... A61P 1/16; A61K 2300/00; A61K 31/09; A61K 31/706
See application file for complete search history.

(56) References Cited

U.S. PATENT DOCUMENTS

| | | | |
|---|---|---|---|
| 10,344,002 B2 | 7/2019 | Zemel et al. | |
| 2019/0060336 A1* | 2/2019 | Huizenga | .............. A23L 33/175 |
| 2021/0205342 A1 | 7/2021 | Dellinger et al. | |

FOREIGN PATENT DOCUMENTS

| | | |
|---|---|---|
| CN | 105012281 A | 11/2015 |
| EP | 2979706 A1 | 2/2016 |
| WO | WO-2016/149277 A1 | 9/2016 |
| WO | WO-2016/200447 A1 | 12/2016 |
| WO | WO-2017/147180 A1 | 8/2017 |
| WO | WO-2018/170389 A1 | 9/2018 |

OTHER PUBLICATIONS

Dellinger et al., "Repeat Dose NRPT (nicotinamide riboside and pterostilbene) Increases NAD+ Levels in Humans Safely and Sustainably: A Randomized, Double-Blind, Placebo-Controlled Study," NPJ Aging and Mechanisms of Disease 3(1):2-7 (2017).
Gariani et al., "Eliciting the Mitochondrial Unfolded Protein Response by Nocotinamide Adenine Dinucleotide Repletion Reverses Fatty Liver Diseases in Mice," Hepatology, 63(4):1190-1204 (2016).
International Search Report and Written Opinion for International Application No. US2018/022854 mailed Jun. 21, 2018.
Lee et al., "Pterostilbene Inhibits Dimethylnitrosamine-Induced Liver Fibrosis in Rats," Food Chemistry, 138(2):802-807 (2012).
Mukherjee et al., "Nicotinamide Adenine Dinucleotide Biosynthesis Promotes Liver Regeneration," Hepatology, 65(2):616-630 (2016).
Teijeiro et al., "Nicotinamide Riboside of IL-17A Signaling Blockers to Prevent Liver Disorders," Oncoscience 4:1-2 (2017).

* cited by examiner

*Primary Examiner* — Pancham Bakshi
(74) *Attorney, Agent, or Firm* — Foley Hoag LLP; Brendan T. Jones; Allison L. Gilder

(57) ABSTRACT

Provided herein are methods and compositions related to treating and/or preventing liver related diseases and disorders and for improving liver health in a subject by administering to the subject (e.g., orally administering to the subject) a composition comprising nicotinamide riboside and/or pterostilbene.

8 Claims, 2 Drawing Sheets

NICOTINAMIDE RIBOSIDE FOR USE IN TREATING OR PREVENTING LIVER DAMAGE

RELATED APPLICATION

This application is a divisional application of U.S. patent application Ser. No. 16/494,581, which is a § 371 national-stage application based on PCT/US18/022854, filed Mar. 16, 2018, which claims the benefit of priority to U.S. Provisional Patent Application Ser. No. 62/472,883, filed Mar. 17, 2017, hereby incorporated by reference in its entirety.

BACKGROUND

Liver damage occurs in a number of acute and chronic clinical conditions, including drug-induced hepatotoxicity, viral infections, vascular injury, autoimmune disease and blunt trauma. In addition, patients subject to inborn errors of metabolism may be at risk for developing liver damage. Symptoms of liver damage occurring as a result of these clinical conditions include, for example, fulminant hepatic failure with cholestasis, hepatic lesions, and liver tissue necrosis and in many instances, the restoration of normal liver function is vital to the survival of patients. Accordingly, there is a great need for new compositions and methods for the treatment and prevention of liver damage and related liver disorders.

SUMMARY

Provided herein are methods and compositions related to treating and/or preventing liver related diseases and disorders and for improving liver health in a subject by administering to the subject (e.g., orally administering to the subject) a composition comprising a compound of Formula I or Formula II (e.g., nicotinamide riboside), and/or a compound of formula III (e.g., pterostilbene).

In certain aspects, the methods and compositions provided herein relate to the treatment and/or prevention of liver damage in a subject by administering to the subject (e.g., orally administering to the subject) a composition comprising a compound of Formula I or Formula II (e.g., nicotinamide riboside) and/or a compound of formula III (e.g., pterostilbene). In certain embodiments, the liver damage is the result of cancer (e.g., liver cancer, bile duct cancer and/or a liver adenoma), cirrhosis, viral infection (e.g., hepatitis A infection, a hepatitis B infection and/or a hepatitis E infection), congenital disorders of metabolism, trauma, autoimmune disease (e.g., autoimmune hepatitis, primary biliary cirrhosis, or primary sclerosing cholangitis), hemochromatosis, hyperoxaluria, oxalosis, Wilson's disease and/or drug-induced hepatotoxicity (e.g., alcohol-induced hepatotoxicity and/or acetaminophen-induced hepatotoxicity).

In certain aspects, the methods and compositions provided herein relate to the treatment and/or prevention of fatty liver in a subject by administering to the subject (e.g., orally administering to the subject) a composition comprising a compound of Formula I or Formula II (e.g., nicotinamide riboside) and/or a compound of formula III (e.g., pterostilbene).

In certain aspects, the methods and compositions provided herein relate to decreasing the serum level of alanine transaminase (ALT) and/or aspartate transaminase (AST) in a subject by administering to the subject (e.g., orally administering to the subject) a composition comprising a compound of Formula I or Formula II (e.g., nicotinamide riboside) and/or a compound of formula III (e.g., pterostilbene). In certain embodiments, the serum level of ALT and/or AST is decreased by at least 0.5 U/L, 1.0 U.L, 1.5 U/L or 2.0 U/L in the subject following administration of the composition.

In certain embodiments of the compositions and methods provided herein, the composition comprises a compound of Formula I or Formula II (e.g., nicotinamide riboside) (e.g., at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg or at least 600 mg of a compound of Formula I or Formula II (e.g., nicotinamide riboside)). In some embodiments, the composition comprises a compound of formula III (e.g., pterostilbene) (e.g., at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg or at least 150 mg of a compound of formula III (e.g., pterostilbene)). In certain embodiments, the composition comprises both a compound of Formula I or Formula II (e.g., nicotinamide riboside) (e.g., at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg or at least 600 mg of a compound of Formula I or Formula II (e.g., nicotinamide riboside)) and a compound of formula III (e.g., pterostilbene) (e.g., at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg or at least 150 mg of a compound of formula III (e.g., pterostilbene)).

In certain embodiments, the method comprises administering a plurality of doses of the composition. In some embodiments, at least 7 doses of the composition are administered. In some embodiments, at least 30 doses of the composition are administered. In some embodiments, at least 60 or more doses of the composition are administered. In some embodiments, each dose comprises at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg or at least 600 mg of a compound of Formula I or Formula II (e.g., nicotinamide riboside). In some embodiments, each dose comprises at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg or at least 150 mg of a compound of formula III (e.g., pterostilbene). In certain embodiments, each dose comprises at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg or at least 600 mg of a compound of Formula I or Formula II (e.g., nicotinamide riboside) at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg or at least 150 mg of a compound of formula III (e.g., pterostilbene).

In certain embodiments, a dose of the composition is administered at regular intervals over a period of time. In some embodiments, a dose of the composition is administered at least once a week. In some embodiments, a dose of the composition is administered at least twice a week. In certain embodiments, a dose of the composition is administered at least three times a week. In some embodiments, a dose of the composition is administered at least once a day. In some embodiments, a dose of the composition is administered at least twice a day. In some embodiments, doses of the composition are administered for at least 1 week, for at least 2 weeks, for at least 3 weeks, for at least 4 weeks, for at least 1 month, for at least 2 months, for at least 3 months, for at least 4 months, for at least 5 months, for at least 6 months or for at least 1 year.

In certain embodiments, the composition is formulated for oral delivery. In some embodiments, the composition is formulated as a pill, a tablet, or a capsule. In some embodiments, the composition is administered orally. In certain embodiments, the composition is self-administered.

DETAILED DESCRIPTION

General

Figure 1:
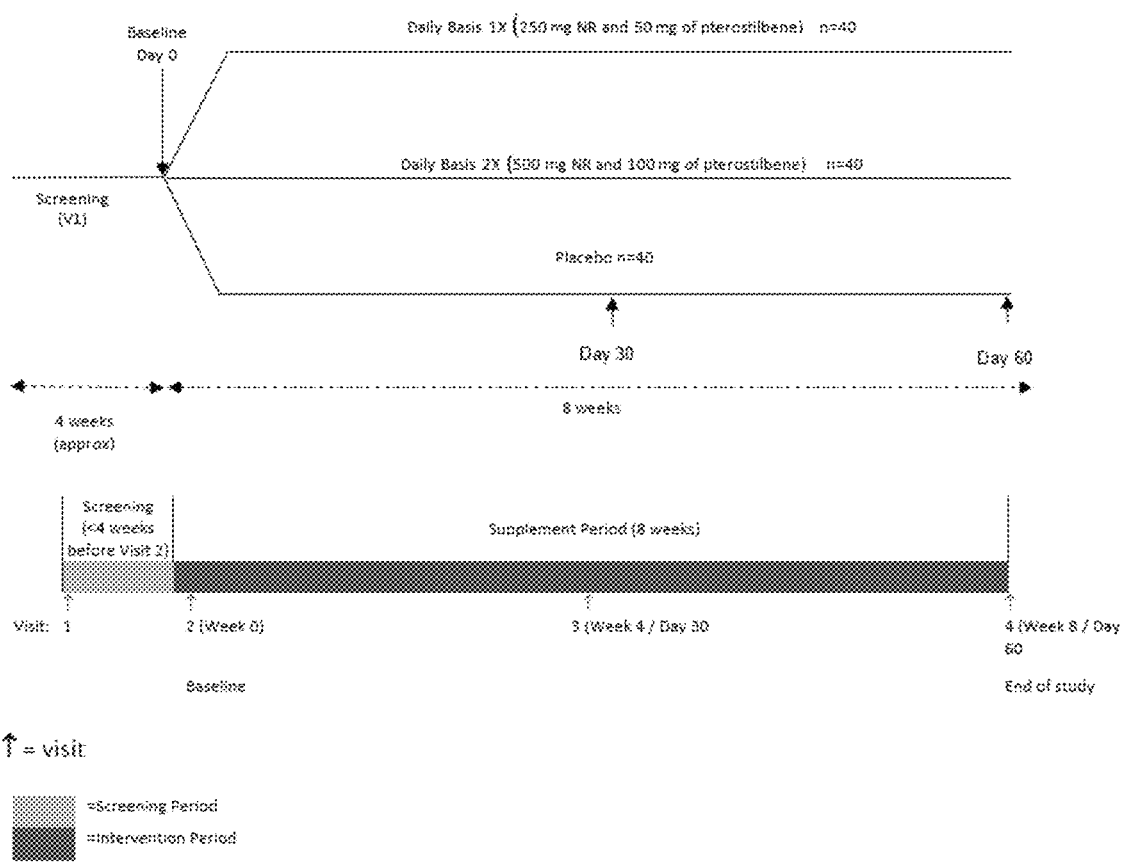
FIG. 1 shows a clinical trial flow diagram depicting the randomized, double-blind, placebo-controlled, three-arm parallel group study described herein. The study consisted of a single eight-week study period. A total of 159 potential subjects were screened to successfully enroll 120 eligible subjects and randomize them 1:1:1 to three arms. Clinic visits occurred at Day 0 (baseline), Day 30 and Day 60. Subjects were asked to fast 12 hours prior to each clinic visit. Each clinic visit consisted of a physical exam including as well as blood draws to evaluate safety and efficacy endpoints of the trial.

Provided herein are methods and compositions related to treating and/or preventing liver related diseases and disorders and for improving liver health in a subject by administering to the subject (e.g., orally administering to the subject) a composition comprising a compound of Formula I or Formula II (e.g., nicotinamide riboside) and/or a compound of formula III (e.g., pterostilbene). In certain aspects, provided herein are methods and compositions related to treating or preventing liver damage and/or fatty liver. In some aspects, provided herein are methods and compositions for decreasing the amount of alanine transaminase (ALT) and/or the amount of aspartate transaminase (AST) in a subject.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering. Administration of a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

The phrase "pharmaceutically-acceptable carrier" as used herein means a pharmaceutically-acceptable material, composition or vehicle, such as a liquid or solid filler, diluent, excipient, or solvent encapsulating material.

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

As used herein, a therapeutic that "prevents" a disorder or condition refers to a compound that, when administered to a statistical sample prior to the onset of the disorder or condition, reduces the occurrence of the disorder or condition in the treated sample relative to an untreated control sample, or delays the onset or reduces the severity of one or more symptoms of the disorder or condition relative to the untreated control sample.

Compositions

Provided herein are pharmaceutical compositions comprising a compound of Formula I or Formula II (e.g., nicotinamide riboside) and/or a compound of formula III (e.g., pterostilbene).

Nicotinamide riboside is a pyridine-nucleoside form of niacin (i.e., vitamin $B_3$) that serves as a precursor to nicotinamide adenine dinucleotide (NAD±). As used herein, "nicotinamide riboside" also includes nicotinamide riboside salts, such as nicotinamide riboside chloride. The chemical structure of nicotinamide riboside is provided below:

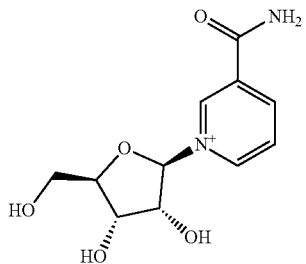 [SMILES: NC(=O)c1ccc[n+]([C@@H]2O[C@H](CO)[C@@H](O)[C@H]2O)c1]

In some embodiments, provided herein are pharmaceutical compositions comprising a compound represented by Formula (I) or a pharmaceutically acceptable salt thereof:

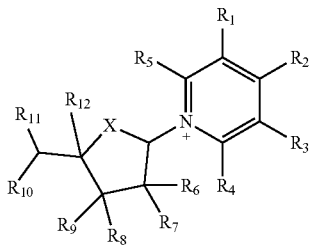

wherein, independently for each occurrence:
$R_1$, $R_2$, and R3 are selected from hydrogen, halogen, —CN, —$NO_2$, —$OR_{14}$, —$N(R_{14})_m$, —$R_{13}$, substituted or unsubstituted ($C_1$-$C_6$)alkyl, cycloalkyl, heterocycloalkyl, aryl, heteroaryl, aralkyl, and heteroaralkyl;
$R_4$ and $R_5$ are selected from hydrogen, halogen, —CN, —$NO_2$, —$OR_{14}$, —$N(R_{14})_m$, substituted or unsubstituted ($C_1$-$C_6$)alkyl, cycloalkyl, heterocycloalkyl, aryl, heteroaryl, aralkyl, and heteroaralkyl;
$R_6$, $R_8$, $R_{11}$, and $R_{12}$ are selected from hydrogen, ($C_1$-$C_6$)alkyl, —(($C_1$-$C_6$)alkylene)$N(R_{14})_m$, —$C(O)((C_1$-$C_6$)alkylene)$N(R_{14})_m$, cycloalkyl, heterocycloalkyl, aryl, heteroaryl, aralkyl, heteroaralkyl, —$OR_{14}$, and —$N(R_{14})_m$;
$R_7$, $R_9$, and $R_{10}$ are selected from —(($C_1$—$C_6$)alkylene)$N(R_{14})_m$, —$OR_{14}$, and —$N(R_{14})_m$;
$R_{13}$ is selected from —$OR_{14}$, —$N(R_{14})_m$, —$C(O)(R_{14})$, —$C(O)(OR_{14})$, —$C(O)N(R_{14})_m$, —$S(O)_2(OR_{14})$, —$S(O)_2(OR_{14})$, and —$S(O)OR_{14}$, and —$S(O)_2N(R_{14})_m$;

$R_{14}$ is selected from hydrogen, ($C_1$-$C_6$)alkyl, cycloalkyl, heterocycloalkyl, aryl, heteroaryl, aralkyl, and heteroaralkyl; and
X is O, S, or $N(R_{14})$;
m is 2 or 3;
provided that at least one of $R_1$, $R_2$, and $R_3$ is $R_{13}$.

In some embodiments, $R_1$ is $R_{13}$. In some embodiments, $R_2$ is $R_{13}$. In some embodiments, $R_3$ is $R_{13}$.

In some embodiments, $R_{13}$ is selected from —$OR_{14}$, —$N(R_{14})_m$, —$C(O)(R_{14})$, —$C(O)(OR_{14})$, and —$C(O)N(R_{14})_m$. In some embodiments, $R_{13}$ is selected from —$C(O)(R_{14})$, —$C(O)(OR_{14})$, and —$C(O)N(R_{14})_m$. In some embodiments, $R_{13}$ is —$C(O)N(R_{14})_m$.

In some embodiments, $R_7$, $R_9$, and $R_{10}$ are each independently —$OR_{14}$ or —$N(R_{14})_m$. In some embodiments, $R_7$, $R_9$, and $R_{10}$ are —$OR_{14}$.

In some embodiments, the compound of formula (I) is represented by Formula (II) or a pharmaceutically acceptable salt thereof:

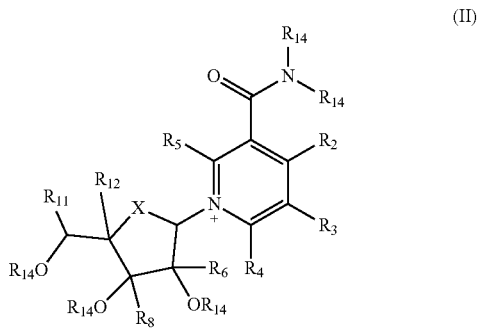

wherein, independently for each occurrence:
$R_2$ and $R_3$ are selected from hydrogen, halogen, —CN, —$NO_2$, —$OR_{14}$, —$N(R_{14})_m$, —$R_{13}$, substituted or unsubstituted ($C_1$-$C_6$)alkyl, cycloalkyl, heterocycloalkyl, aryl, heteroaryl, aralkyl, and heteroaralkyl;
$R_4$ and $R_5$ are selected from hydrogen, halogen, —CN, —$NO_2$, —$OR_{14}$, —$N(R_{14})_m$, substituted or unsubstituted ($C_1$-$C_6$)alkyl, cycloalkyl, heterocycloalkyl, aryl, heteroaryl, aralkyl, and heteroaralkyl;
$R_6$, $R_8$, $R_{11}$, and $R_{12}$ are selected from hydrogen, —$OR_{14}$, —$N(R_{14})_m$, substituted or unsubstituted ($C_1$-$C_6$)alkyl, —(($C_1$-$C_6$)alkylene)$N(R_{14})_m$, —$C(O)((C_1$-$C_6$)alkylene)$N(R_{14})_m$, cycloalkyl, heterocycloalkyl, aryl, heteroaryl, aralkyl, and heteroaralkyl;
$R_{13}$ is selected from —$OR_{14}$, —$N(R_{14})_m$, —$C(O)(R_{14})$, —$C(O)(OR_{14})$, —$C(O)N(R_{14})_m$, —$S(O)_2(OR_{14})$, —$S(O)OR_{14}$, and —$S(O)_2N(R_{14})_m$;
$R_{14}$ is selected from hydrogen, ($C_1$-$C_6$)alkyl, cycloalkyl, heterocycloalkyl, aryl, heteroaryl, aralkyl, and heteroaralkyl; and
m is 2 or 3.

In some embodiments of the compounds of formula (I) or (II), $R_1$, $R_2$, and $R_3$ are each independently, if present, selected from hydrogen, halogen, —CN, —$NO_2$, —$OR_{14}$, —$N(R_{14})_m$, —$R_{13}$, and substituted or unsubstituted ($C_1$-$C_6$) alkyl. In some embodiments, $R_1$, $R_2$, and $R_3$ are each independently, if present, selected from hydrogen, —$OR_{14}$, —$N(R_{14})_m$, and unsubstituted ($C_1$-$C_6$)alkyl. In some embodiments, $R_1$, $R_2$, and $R_3$ are each independently, if present, selected from substituted or unsubstituted ($C_1$-$C_6$) alkyl, cycloalkyl, heterocycloalkyl, aryl, heteroaryl, aralkyl, and heteroaralkyl. In some embodiments, $R_1$, $R_2$, and $R_3$ are each independently, if present, hydrogen.

In some embodiments of the compounds of formula (I) or (II), $R_4$ and $R_5$ are each independently selected from hydrogen, halogen, —CN, —$NO_2$, —$OR_{14}$, —$N(R_{14})_m$, and substituted or unsubstituted ($C_1$-$C_6$)alkyl. In some embodiments, $R_4$ and $R_5$ are each independently selected from hydrogen, —$OR_{14}$, —$N(R_{14})_m$, and unsubstituted ($C_1$-$C_6$) alkyl. In some embodiments, $R_4$ and $R_5$ are each independently selected from substituted or unsubstituted ($C_1$-$C_6$) alkyl, cycloalkyl, heterocycloalkyl, aryl, heteroaryl, aralkyl, and heteroaralkyl. In some embodiments, $R_4$ and $R_5$ are each hydrogen.

In some embodiments of the compounds of formula (I) or (II), $R_6$, $R_8$, $R_{11}$, and $R_{12}$ are selected from hydrogen, —$OR_{14}$, —$N(R_{14})_m$, unsubstituted ($C_1$-$C_6$)alkyl, —(($C_1$-$C_6$) alkylene)$N(R_{14})_m$, —C(O)(($C_1$-$C_6$)alkylene)$N(R_{14})_m$, cycloalkyl, heterocycloalkyl, aryl, heteroaryl, aralkyl, and heteroaralkyl. In some embodiments, $R_6$, $R_8$, $R_{11}$, and $R_{12}$ are each independently selected from hydrogen, —$OR_{14}$, —$N(R_{14})_m$, unsubstituted ($C_1$-$C_6$)alkyl, $C_6$)alkylene) $N(R_{14})_m$, and —C(O)(($C_1$-$C_6$)alkylene)$N(R_{14})_m$. In some embodiments, $R_6$, $R_8$, $R_{11}$, and $R_{12}$, are each independently selected from hydrogen, —$OR_{14}$, and —$N(R_{14})_m$. In some embodiments, $R_6$, $R_8$, $R_{11}$, and $R_{12}$ are each independently selected from unsubstituted ($C_1$-$C_6$)alkyl, cycloalkyl, heterocycloalkyl, aryl, heteroaryl, aralkyl, and heteroaralkyl. In some embodiments, $R_6$, $R_8$, $R_{11}$, and $R_{12}$ are each hydrogen.

In some embodiments, $R_7$, $R_9$, and $R_{10}$ are each independently —$OR_{14}$ or —$N(R_{14})_m$. In some embodiments, $R_7$, $R_9$, and $R_{10}$ are each —$OR_{14}$. In some embodiments, $R_7$, $R_9$, and $R_{10}$ are each —OH.

In some embodiments of the compounds of formula (I) or (II), $R_{14}$ is hydrogen or ($C_1$-$C_6$)alkyl.

In some embodiments of the compounds of formula (I) or (II), X is O or N($R_{14}$). In some embodiments, X is O.

In some embodiments of the compounds of formula (I) or (II), the compound is

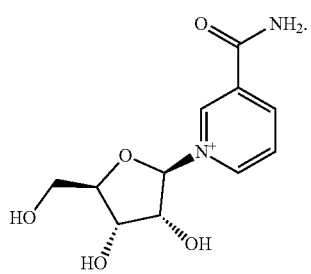 [SMILES: NC(=O)c1ccc[n+]([C@@H]2O[C@H](CO)[C@@H](O)[C@H]2O)c1]

Pterostilbene is a stilbenoid and an analog of polyphenol reservatrol that has better bioavailability due to the presence of two methoxy groups that allow it to have increased lipophilic and oral absorption as well as a longer half-life due to reduced oxidation. The chemical structure of pterostilbene is provided below:

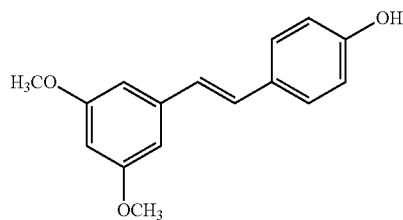 [SMILES: COc1cc(/C=C/c2ccc(O)cc2)cc(OC)c1]

In some embodiments, provided herein are pharmaceutical compositions comprising a compound represented by Formula (III) or a pharmaceutically acceptable salt thereof:

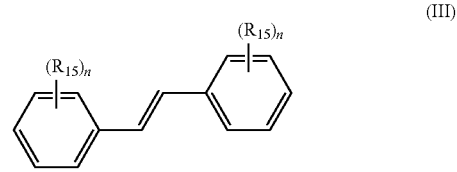

wherein, independently for each occurrence:
$R_{15}$ is selected from halogen, —CN, —$NO_2$, —$OR_{16}$, —$N(R_{16})_p$, —$S(O)_2(OR_{16})$, —$S(O)OR_{16}$, substituted or unsubstituted ($C_1$-$C_6$)alkyl, cycloalkyl, heterocycloalkyl, aryl, heteroaryl, aralkyl, and heteroaralkyl;
$R_{16}$ is selected from hydrogen, ($C_1$-$C_6$)alkyl, cycloalkyl, heterocycloalkyl, aryl, heteroaryl, aralkyl, and heteroaralkyl;
n is an integer from 0 to 5; and
p is 2 or 3;
provided that at least one n is 1; and at least one $R_{15}$ is —$OR_{16}$; provided that the compound of formula (III) is not

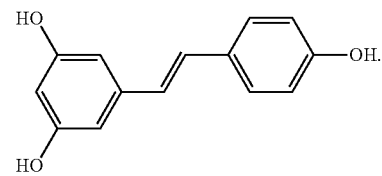 [SMILES: Oc1ccc(/C=C/c2cc(O)cc(O)c2)cc1]

In some embodiments of the compounds of formula (III), $R_{15}$ is selected from, halogen, —CN, —$NO_2$, —$OR_{16}$, —$N(R_{16})_p$, and substituted or unsubstituted ($C_1$-$C_6$)alkyl. In some embodiments, $R_{15}$ is selected from —$OR_{16}$, —$N(R_{16})_p$, and unsubstituted ($C_1$-$C_6$)alkyl. In some embodiments, $R_{15}$ is selected from substituted or unsubstituted ($C_1$-$C_6$)alkyl, cycloalkyl, heterocycloalkyl, aryl, heteroaryl, aralkyl, and heteroaralkyl. In some embodiments, $R_{15}$ is —$OR_{16}$. In some embodiments, $R_{15}$ is —$OR_{16}$; and $R_{16}$ is hydrogen or ($C_1$-$C_6$)alkyl. In some embodiments, $R_{15}$ is —$OR_{16}$; and $R_{16}$ is ($C_1$-$C_6$)alkyl, cycloalkyl, heterocycloalkyl, aryl, heteroaryl, aralkyl, and heteroaralkyl. In some embodiments, $R_{15}$ is —$OR_{16}$; and $R_{16}$ is ($C_1$-$C_6$)alkyl. In some embodiments, $R_{15}$ is —$OR_{16}$; and $R_{16}$ is ($C_1$-$C_6$)alkyl, cycloalkyl, or heterocycloalkyl.

In some embodiments, n is 1, 2, or 3. In some embodiments, n is 1 or 2.

In some embodiments, p is 2. In some embodiments, p is 3.

In one aspect, the provided herein are pharmaceutically acceptable compositions which comprise a therapeutically-effective amount of one or more of the compounds described herein (e.g., nicotinamide riboside and/or pterostilbene), formulated together with one or more pharmaceutically acceptable carriers (additives) and/or diluents. In another aspect, the agents described herein can be administered as such, or administered in mixtures with pharmaceutically acceptable carriers and can also be administered in conjunction with other agents. Conjunctive therapy thus includes sequential, simultaneous and separate, or co-administration of one or more compounds of the invention, wherein the therapeutic effects of the first administered has not entirely disappeared when the subsequent compound is administered.

As described in detail below, the pharmaceutical compositions described herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; or (3) sublingually.

In some embodiments, the composition comprises additional agents. For example, the composition may comprise a nutritional agent, such as an antioxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations of the compounds described herein may be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the agent which produces a therapeutic effect.

In certain embodiments, a formulation described herein comprises an excipient, including, but not limited to, cyclodextrins, liposomes, micelle forming agents, e.g., bile acids, and polymeric carriers, e.g., polyesters and polyanhydrides; and an agent of the invention. In some embodiments, an aforementioned formulation renders orally bioavailable an agent of the invention. Methods of preparing these formulations or compositions may include the step of bringing into association a compound of the invention with the carrier and, optionally, one or more accessory ingredients.

Liquid dosage forms for oral administration of the formulations provided herein include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations provided herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. A compound of the invention may also be administered as a bolus, electuary, or paste.

In solid dosage forms of the invention for oral administration (e.g., capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions described herein may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Pharmaceutical compositions provided herein suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Therapeutic Methods

Provided herein are methods of preventing or treating liver damage and/or fatty liver in a subject by administering to the subject (e.g., a subject in need thereof) a composition disclosed herein (i.e., a composition comprising a compound of Formula I or Formula II (e.g., nicotinamide riboside) and/or a compound of formula III (e.g., pterostilbene)).

In some embodiments, the subject may have or be predisposed to liver damage and/or fatty liver. Liver damage may result from any condition that causes the cells of the liver (i.e., hepatocytes) to die or otherwise not function normally. Examples of conditions that may cause liver damage include, but are not limited to, cancer (e.g., liver cancer, bile duct cancer, or a liver adenoma), trauma, congenital metabolic disorders (e.g., genetic metabolic disorders resulting in an enzyme deficiency), vascular injury, cirrhosis, a viral infection (e.g., hepatitis A, hepatitis B, hepatitis E), an autoimmune disease (e.g., autoimmune hepatitis, primary biliary cirrhosis, or primary sclerosing cholangitis), hemochromatosis, hyperoxaluria, oxalosis, Wilson's disease, or drug-induced hepatotoxicity (e.g., alcohol-induced hepatotoxicity or acetaminophen-induced hepatotoxicity). Fatty liver may be caused by any condition that causes fat accumulation of liver. These conditions may be, but are not limited to, non-alcoholic fatty liver disease or alcoholic liver disease.

Disclosed herein are methods of treating or preventing age-related symptoms or diseases comprising administering a composition disclosed herein. Provided herein are methods of decreasing the amount of alanine transaminase (ALT) and/or aspartate transaminase (AST) in a subject comprising administering to the subject a composition provided herein. AST and ALT are reasonably sensitive indicators of liver damage or injury from different types of diseases or conditions, and they are often measured in liver tests or liver blood tests. Elevated levels of AST and ALT are associated with liver damage and liver malfunction. In some embodiments, ALT is decreased in the subject by at least 0.1 U/L, at least 0.2 U/L, at least 0.3 U/L, at least 0.4 U/L, at least 0.5 U/L, at least 0.6 U/L, at least 0.7 U/L, at least 0.8 U/L, at least 0.9 U/L, at least 01.0 U/L, 1.1 U/L, at least 1.2 U/L, at least 1.3 U/L, at least 1.4 U/L, at least 1.5 U/L, at least 1.6 U/L, at least 1.7 U/L, at least 1.8 U/L, at least 1.9 U/L, at least 2.0 U/L, 2.1 U/L, at least 2.2 U/L, at least 2.3 U/L, at least 2.4 U/L, at least 2.5 U/L, at least 2.6 U/L, at least 2.7 U/L, at least 2.8 U/L, at least 2.9 U/L, at least 3.0 U/L, at least 3.5 U/L, 4.0 U/L, at least 4.5 U/L, or at least 5.0 U/L after administration of the composition. In some embodiments, the ALT is decreased by at least 0.1 U/L, at least 0.2 U/L, at least 0.3 U/L, at least 0.4 U/L, at least 0.5 U/L, at least 0.6 U/L, at least 0.7 U/L, at least 0.8 U/L, at least 0.9 U/L, at least 01.0 U/L, 1.1 U/L, at least 1.2 U/L, at least 1.3 U/L, at least 1.4 U/L, at least 1.5 U/L, at least 1.6 U/L, at least 1.7 U/L, at least 1.8 U/L, at least 1.9 U/L, at least 2.0 U/L, 2.1 U/L, at least 2.2 U/L, at least 2.3 U/L, at least 2.4 U/L, at least 2.5 U/L, at least 2.6 U/L, at least 2.7 U/L, at least 2.8 U/L, at least 2.9 U/L, at least 3.0 U/L, at least 3.5 U/L, 4.0 U/L, at least 4.5 U/L, or at least 5.0 U/L after administration of the composition.

Nicotinamide adenine dinucleotide (NAM is a coenzyme that participates in many metabolic reactions. NAD+ plays an important role in transcription regulation, longevity, and age-associated diseases. NAD+ levels decrease with age, while increased NAD+levels are associated with robust health. In some embodiments, provided herein are methods of increasing the amount of NAD+ of a subject by administering a composition disclosed herein. NAD+ may increase by at least 1.0 µg/mL, at least 2.0 µg/mL, at least 3.0 µg/mL, at least 4.0 µg/mL, at least 5.0 µg/mL, at least 6.0 µg/mL, at least 7.0 µg/mL, at least 8.0 µg/mL, at least 9.0 µg/mL, at least 10.0 µg/mL, at least 11.0 µg/mL, at least 12.0 µg/mL, at least 13.0 µg/mL, at least 14.0 µg/mL, at least 15.0 µg/mL, at least 16 µg/mL, at least 17 µg/mL, at least 18 µg/mL, at least 19 µg/mL, at least 20 µg/mL, at least 21 µg/mL, at least 22 µg/mL, at least 23 µg/mL, at least 24 µg/mL, at least 25 µg/mL, at least 26 µg/mL, at least 27 µg/mL, at least 28 µg/mL, at least 29 µg/mL, or at least 30 µg/mL after administration of the composition.

Provided herein are methods of decreasing blood pressure (e.g., diastolic blood pressure) of a subject by administering a composition herein. In some embodiments, the subject's diastolic blood pressure decreases by at least 1 mmHg, at least 1.5 mmHg, at least 2 mmHg, at least 2.5 mmHg, at least 3 mmHg, at least 3.5 mmHg, at least 4.0 mmHg, at least 4.5 mmHg, or at least 5 mmHg after administration of the composition.

Actual dosage levels and administration regimen of the compositions disclosed herein may be varied so as to obtain an amount of a compound of Formula I or Formula II (e.g., nicotinamide riboside) and/or a compound of formula III (e.g., pterostilbene) that is effective to achieve the desired therapeutic response for a particular patient, composition, and mode of administration, without being toxic to the patient.

In some embodiments, administration of the composition comprises administration of the composition in one or more dose(s). In some embodiments, administration of the composition comprises administration of the composition in one or more, five or more, ten or more, twenty or more, thirty or more, forty or more, fifty or more, one hundred or more, or one thousand or more dose(s). In some embodiments, the dose comprises at least 25 mg, at least 50 mg, at least 75 mg, at least 100 mg, at least 125 mg, at least 150 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 550 mg, at least 600 mg, at least 650 mg, at least 700 mg, at least 750 mg, at least 800 mg, or at least 850 mg of a compound of Formula I or Formula II (e.g., nicotinamide riboside). In some embodiments, the dose comprises at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 90 mg, at least 95 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, or at least 250 mg of a compound of formula III (e.g., pterostilbene).

The compositions disclosed herein may be administered over any period of time effective to achieve the desired therapeutic response for a particular patient, composition, and mode of administration, without being toxic to the patient. The period of time may be at least 1 day, at least 10 days, at least 20 days, at least 30, days, at least 60 days, at least three months, at least six months, at least a year, at least three years, at least five years, or at least ten years. The dose may be administered when needed, sporadically, or at regular intervals. For example, the dose may be administered monthly, weekly, biweekly, triweekly, once a day, or twice a day.

EXEMPLIFICATION

A human clinical trial was conducted in accordance of with the ethical principles that their origins in the Declaration of Helsinki and its subsequent amendments (clinical trials.gov identifier NCT02678611). The study was reviewed by the Natural and Non-prescription Health Products Directorate (NNHPD), Health Canada and a research ethics board. Notice of authorization was granted on Dec. 11, 2015 by the NNHPD, Ottawa, Ontario and unconditional approval was granted on Dec. 23, 2015 by the Institutional Review Board (IRB Services, Aurora, Ontario).

The study was a randomized, double-blinded, placebo controlled study with a 30-day follow up period that was carried out at 3 sites, London, Ontario (Canada); Orlando, Florida; and Irvine, California. All participants that met inclusion and not exclusion criteria at screening were randomized into three groups: placebo, Basis (an exemplary composition comprising nicotinamide riboside and pterostilbene) at recommended dose (Basis 1X) and Basis at twice the recommended dose (Basis 2X).

The objective of this study was to evaluate the safety CBC, electrolytes (Na, K, Cl), kidney function (creatinine), liver function (AST, ALT, GGT and bilirubin) and tolerability of two doses of Basis (nicotinamide riboside and pterostilbene) supplements in elderly participants after eight weeks of treatment. Secondary objectives of the study evaluated the potential benefits of Basis in increasing blood NAD+ and effecting lipid metabolism.

Participants

The inclusion criteria were as follows: males or females 60 to 80 (inclusive) years of age with a Body Mass Index (BMI) between 18 to 35 kg/m$^2$ (±1 kg/m$^2$). Participants agreed to avoid taking vitamin $B_3$ (Niacin, Nicotinic acid or nicotinamide) supplements or multivitamins 14 days prior to randomization and for the duration of the study period. Participants were healthy as determined by laboratory results, medical history and physical examination. Individuals gave voluntary, written, informed consent to participate in the study.

Individuals were excluded if they had: unstable medical conditions, history of any significant chronic disease or any clinically active illness within 3 months of study entry, history of renal or liver impairment, any endocrine, inflammatory, cardiovascular, gastro-intestinal, neurological, psychiatric, neoplastic or metabolic disease, significant or untreated medical disorders including recent myocardial ischemia or infarction, unstable angina, uncontrolled hypertension, AIDS, malignancy, epilepsy, and recent cerebrovascular disease, recently experienced a traumatic injury, infections or undergone surgery, history of pellagra or niacin deficiency, currently taking lipid lowering drugs, use of natural health products containing nicotinamide riboside within 14 days prior to randomization and during the study. History of, or current diagnosis of any cancer (except for successfully treated basal cell carcinoma) diagnosed less than five years prior to screening were also excluded. Volunteers with cancer in full remission more than five years after diagnosis are acceptable. Subjects were also excluded if they had participated in any clinical trial with an investigational medicinal product within the past three months prior to the first dose in the current study, alcohol use of greater than 2 standard alcoholic drinks per day, history of alcoholism or drug abuse within one year prior to screening, history of significant allergies, allergy or sensitivity to any of the investigational product ingredients, or used medicinal marijuana. Clinically significant abnormal laboratory results at screening as well as individuals who are cognitively impaired and/or who are unable to give informed consent were also excluded. Any other condition which in the Investigator's opinion may adversely affect the participant's ability to complete the study or its measures or which may pose significant risk to the participant were also excluded. Clinical significance of disease was assessed by the Qualified Investigator and eligibility determined.

Intervention

The investigational product Basis contained nicotinamide riboside and pterostilbene. Non-dietary ingredients were microcrystalline cellulose, silicon dioxide, magnesium stearate, gelatin. Placebo capsules consisted of microcrystalline cellulose, silicon dioxide, magnesium stearate, gelatin. During the intervention period two groups received the investigational supplement, Basis (containing 125 mg nicotinamide riboside and 25 mg pterostilbene per capsule) while the third group received a placebo capsule. All subjects took 4 capsules daily. All participants received 2 bottles containing capsules (Bottle A and Bottle B) and instructed to take 2 capsules from each bottle daily. Each arm was provided with bottles containing the following: Basis 1X:

Bottle A=Basis (125 mg capsules), Bottle B=Placebo (125 mg capsules). Basis 2X: Bottle A=Basis (125 mg capsules), Bottle B=Basis (125 mg capsules) Placebo: Bottle A=Placebo, Bottle B=Placebo.

Sample Size

The planned sample size for this study was 120 participants, with 40 participants randomized to each of the three arms.

Randomisation and Blinding

A randomization schedule was prepared using block randomisation by an unblinded person at the study site who was not involved in study assessment. The investigational supplement, Basis, and placebo were sealed in identical bottles, which were labelled per the requirements of ICH-GCP guidelines and applicable local regulatory guidelines. The placebo capsules mimicked the size, shape and colour of the investigational product capsules. The investigational supplement was labelled by unblinded personnel at KGK Synergize who were not involved in study assessments. All clinic staff involved in product dispensing, collection of data and monitoring charts and analysis of outcomes remained blinded for the duration of the study.

Clinic Visits

Eligible volunteers will return to the clinic in the morning, after 12 hours fast (nothing to eat or drink except water) for baseline assessments. A physical exam will be conducted. Weight will be measured and BMI calculated. Resting blood pressure and heart rate will be measured. Fasting blood samples will be collected for fasting glucose, lipid panel, hs-CRP, CBC, electrolytes (Na, K, Cl), creatinine, AST, ALT, GGT, bilirubin, PBMC, and NAD+analysis.

Sample Collection and Preparation for NAD+ Analysis

Fasting blood samples were collected analysis of nicotinamide adenine dinucleotide (NAD+). 4 mL of whole blood was collected in sodium citrate tubes and the tubes inverted gently four times and the placed immediately on wet ice. 1 mL of 0.5 M Perchloric acid was aliquoted to 4 cryogenic screw cap bottles with seals and placed on wet ice. Whole blood aliquots of 0.1 mL of were transferred to each cryovial and gently inverted 4 times and then placed on wet ice. The screw caps replaced and tubes kept on ices and stored at −80° C. till analyzed.

NAD+ Analysis

Samples were thawed and centrifuged at 13,000 rpm for 5 minutes at room temperature. 0.11 mL of supernatant was transferred to 2.0 mL glass HPLC injection vial. Then 100 μL of 0.5 M PCA in water was added. 50 μL of internal standard solution (5 μg/mL of $^{13}C_5$-nicotinamide adenine dinucleotide in 0.5 M PCA) was then added followed by 0.5 mL of 0.5 M PCA in water. Samples were capped and vortexed for 20 seconds. 10 μL was then injected onto the LC/MS/MS. Mobile phase A was 0.5% formic acid in water and mobile phase B was 0.5% formic acid in acetonitrile. A linear gradient of 0-100% B was run and the mass spec was set on positive ion mode looking for the transitions of 664.4→524.0 (NAD+) and 669.4→529.3 (the internal standard).

Statistics

Numerical efficacy endpoints were formally tested for significance between groups by Analysis of Covariance (ANCOVA). The dependent variable was the value at end-of-study (day 60); the factor was the product group, and the value at baseline (day 0) was the covariate. When the omnibus ANCOVA and ANOVA p-values suggested at least one mean difference was present, pairwise comparisons using the Tukey-Kramer procedure were run. Significant efficacy of Investigational Products, relative to placebo, was inferred if the pairwise comparisons were significantly different from zero ($p \leq 0.05$).

Intractably non-normal data was formally tested for significance between groups by the Kruskal-Wallis test. When the omnibus Kruskal-Wallis p-values suggested at least one mean difference was present, pairwise comparisons using the Bonferroni adjusted Mann-Whitney tests were run. Significant efficacy of Investigational Products, relative to placebo, was inferred if the pairwise comparisons were significantly different from zero ($p \leq 0.05$). A within group analysis on efficacy endpoints was done using a Student's paired samples t-test or, in instances of intractable non-normality, Wilcoxon sign rank test. No changes in analysis were made after unblinding occurred.

Trial Overview

Safety and efficacy of Basis a supplement combining nicotinamide riboside and pterostilbene, was investigated in a population of 120 participants in a randomized double-blind placebo-controlled dose clinical trial. This trial consisted of three-arms of 40 healthy subjects aged 60-80 years each: 1) placebo, 2) Basis at recommended dose (Basis 1X; 250 mg of NR plus 50 mg of pterostilbene), 3) Basis at double dose (Basis 2X; 500 mg of NR plus 100 mg of pterostilbene). Each subject took their assigned treatment orally, at breakfast, each day for 8 weeks. Blood was taken at baseline, at 4 weeks and at 8 weeks to evaluate safety and efficacy in raising NAD+levels in whole blood with a 30-day follow-up after supplementation was stopped. A schematic of the study is shown in FIG. 1.

All participants were analysed in the Intention-to-Treat Population, with 38 participants in the Basis 1X group, 40 in the Basis 2X group and 40 in the placebo group. One hundred and thirteen participants were analysed in the Per Protocol Population, with 33 participants in the Basis 2X group, 40 in the Basis 1X group and 40 in the placebo group. Seven participants were removed from the Per Protocol analysis; one participant was incorrectly enrolled into the study, three participants withdrew consent, two participants had low investigational product compliance (compliance less than 70%) and one participant was not compliant to study procedures.

At randomization participants were well matched between groups and compliance in all groups exceeded 94%. The ITT population was used for all analysis except NAD+, where the PP population was analyzed to eliminate error from non-compliance.

Demographics of participants in the Basis 1X, Basis 2X and placebo group were well matched for age, gender, BMI, smoking status, race and ethnicity. See Table 1 below.

TABLE 1

| Demographics for Participants Enrolled in the Study (N = 120). | | | | | |
|---|---|---|---|---|---|
| | All Participants (N = 120) | Placebo (N = 40) | Basis 1X (N = 40) | Basis 2X (N = 40) | P Value $^\sigma$ |
| Age (Years) | | | | | |
| Mean ± SD | 66.8 ± 5.2 | 66.4 ± 5.3 | 67.5 ± 5.1 | 66.3 ± 5.3 | 0.494 § |
| BMI (kg/m$^2$) | | | | | |
| Mean ± SD | 27.6 ± 4.1 | 28.0 ± 4.1 | 27.9 ± 4.1 | 26.9 ± 4.0 | 0.424 § |
| Gender [n (%)] | | | | | |
| Female | 82 (68%) | 24 (60%) | 30 (75%) | 28 (70%) | 0.389 |
| Male | 38 (32%) | 16 (40%) | 10 (25%) | 12 (30%) | |
| Alcohol Use [n (%)] | | | | | |
| None | 11 (9%) | 7 (18%) | 2 (5%) | 2 (5%) | |
| Occasionally | 23 (19%) | 7 (18%) | 8 (20%) | 8 (20%) | 0.417 |
| Weekly | 48 (40%) | 15 (38%) | 14 (35%) | 19 (48%) | |
| Daily | 38 (32%) | 11 (28%) | 16 (40%) | 11 (28%) | |
| Smoking Status [n (%)] | | | | | |
| Current Smoker | 8 (7%) | 3 (8%) | 3 (8%) | 2 (5%) | 1.000 |
| Ex-Smoker | 39 (32%) | 13 (32%) | 13 (32%) | 13 (32%) | |
| Non-Smoker | 73 (61%) | 24 (60%) | 24 (60%) | 25 (62%) | |
| Race [n (%)] | | | | | |
| Black or African American | 2 (2%) | 2 (5%) | 0 (0%) | 0 (0%) | |
| Eastern European White | 9 (8%) | 4 (10%) | 3 (8%) | 2 (5%) | 0.662 |
| Hispanic or Latino | 3 (2%) | 1 (2%) | 1 (2%) | 1 (2%) | |
| Other | 2 (1%) | 1 (2%) | 1 (0%) | 0 (0%) | |
| Western European White | 104 (87%) | 32 (80%) | 35 (88%) | 37 (92%) | |

Max, maximum; Min, minimum; N, number; %, percentage; SD, standard deviation.
§ Between group comparisons were made using ANOVA (no adjustment for baseline)
$^\sigma$ Between group comparisons were made using the Chi-Squared test
Probability values P ≤ 0.05 are statistically significant.

Of 120 randomized participants in the safety population, 87% identified themselves as western European white, between 60 and 79 years of age with a BMI of 18.7 to 35.8 kg/m$^2$. Sixty-one percent were non-smokers and 68% were female. Use of alcohol was generally evenly distributed between the participants with 91% being occasional, weekly and daily users (Table 1).

Adverse Events

A total of 66 adverse events were reported by 45 participants. Of these, 18 AEs were reported by 13 participants in the placebo, 25 reported by 15 participants in the Basis 1X, and 23 reported by 17 participants in the Basis 2X group. There was 1 AE mild in intensity assessed as possibly related (pruritus) to the placebo product, 1 AE mild in intensity assessed as possibly related to Basis 1X (nausea) and 5 AEs (moderate fatigue, mild headache, moderate dyspepsia, moderate abdominal discomfort and mild diarrhoea) reported by 5 participants in the Basis 2X group ranging assessed as possibly related to Basis 2X. See Table 2 below. One AE (severe diarrhea) was assessed as probably related to Basis 2X. All other AEs were classified as unlikely or not related to the investigational product. All participants reporting AEs recovered and there were no serious adverse events reported during this clinical study.

TABLE 2

| Total Number of Possibly, Probably, or Most Probably Related AEs and Number of Participants Experiencing at Least One AE Separated by System Organ Class Category | | | | | | | |
|---|---|---|---|---|---|---|---|
| | Placebo (N = 40) | | Basis 1X (N = 40) | | Basis 2X (N = 40) | | |
| | Number of AEs n | Participants Experiencing AEs n (%) | Number of AEs n | Participants Experiencing AEs n (%) | Number of AEs n | Participants Experiencing AEs n (%) | Between Group P-Value $^\sigma$ |
| Gastrointestinal disorders | 0 | 0 (0%) | 1 | 1 (2.5%) | 3 | 3 (7.5%) | — |
| General disorders and administration site conditions | 0 | 0 (0%) | 0 | 0 (0%) | 1 | 1 (2.5%) | — |
| Nervous system disorders | 0 | 0 (0%) | 0 | 0 (0%) | 1 | 1 (2.5%) | — |
| Skin and subcutaneous tissue disorders | 1 | 1 (2.5%) | 0 | 0 (0%) | 0 | 0 (0%) | — |
| Overall Adverse Events | 1 | 1 (2.5%) | 1 | 1 (2.5%) | 5 | 5 (12.5%) | 0.088 | n, number.
$^\sigma$ Between group comparisons were made using the Chi-Squared test Basis increases NAD+

Figure 2:
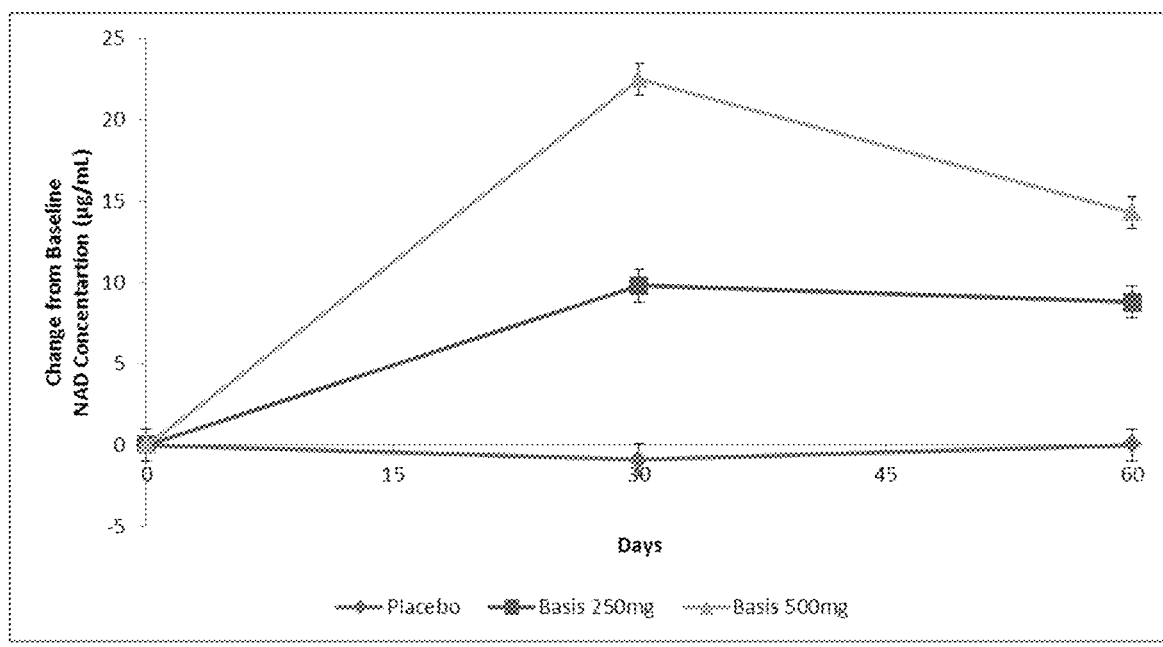
FIG. 2 shows that administration of an exemplary composition comprising nicotinamide riboside and pterostilbene (Basis) to a subject causes an increase in NAD+ levels in the subject. Total NAD+ levels were measured in whole blood from all subjects at day 0 (baseline), day 30 and day 60. The graph depicts NAD+ concentration (µg/ml) for Placebo (circles), Basis 1X (squares) and Basis 2X (triangles). Data shown is the mean±standard deviation for each arm.

Whole blood was collected at baseline, day 30 and day 60 from all subjects for subsequent NAD+ analysis. Collection was at pH 5, which led to red blood cell lysis but preserved NAD+ for analysis. We developed a GLP-compliant method to analyze NAD+ from human whole blood lysates by LC-MS/MS. As shown in FIG. 2, the placebo group showed no increase of NAD+ over the 60-day treatment period. However, NAD+ did significantly increase in a dose-dependent manner at 30 days with Basis 1X increasing NAD+ levels by ~40% and Basis 2X increasing NAD+ levels by ~90% (FIG. 2; Table 3). The 40% increase in NAD+ level observed in the Basis 1X group was sustained at 60 days. The increase in NAD+ levels seen in the Basis 2X group was sustained at ~55% over baseline at 60 days. This increase was still significantly higher than the Basis 1X group at 60 days (FIG. 2; Table 3). The within group increases in the Basis 1X and Basis 2X groups at day 30 and day 60 were highly significant, as were the differences between groups at those time points (Table 3). Thus, Basis increased NAD+ levels in a sustained way.

TABLE 3

Basis increases NAD+

| | Placebo Mean ± SD (n) | Basis 1X Mean ± SD (n) | Basis 2X Mean ± SD (n) | Between Group P-Value |
|---|---|---|---|---|
| | | NAD Concentration (µg/mL) | | |
| Day 0 Baseline | 22.0 ± 8.1 (40) | 22.5 ± 11.9 (39) | 23.8 ± 9.0 (38) | 0.619$^\lambda$ § |
| Day 30 | 21.1 ± 8.6 (40) | 32.2 ± 13.4 (40) | 45.8 ± 20.8 (38) | <0.001$^\lambda$ § |
| Day 60 End of Study | 22.0 ± 7.8 (40) | 31.5 ± 16.3 (40) | 37.2 ± 16.7 (38) | <0.001$^\lambda$ § |
| Change from Day 0 to Day 30 | −0.9 ± 80.8 (40) | 9.8 ± 15.6 (39) $^a$ | 22.0 ± 22.8 (38) $^a$ | <0.001$^\lambda$ Δ |
| Change from Day 0 to Day 60 | 0.0 ± 11.2 (40) | 8.8 ± 16.1 (39) $^a$ | 13.3 ± 19.4 (38) $^a$ | <0.001$^\lambda$ Δ |

§ Between group comparison were made using ANOVA.
Δ Between group comparisons were made using ANCOVA adjusting for baseline.
$^\lambda$ The square root transformation was required to achieve normality
$^a$ denotes significant difference compared to placebo as assessed by the Tukey-Kramer post-hoc test.

Basis 1X and Liver Enzymes

Liver enzymes in blood were also determined as a measure of health of that organ. Liver tests were within normal ranges at baseline for all subjects. There were no changes in the liver function tests for any group (placebo, Basis 1X or Basis 2X) except that a significant decrease was observed in the ALT (alanine transaminase) test at 30 and 60 days within the Basis 1X as compared to baseline (Table 4). A similar trend that did not reach significance was also observed for AST (aspartate transaminase). Since the presence of liver enzymes in the blood indicates defects in liver health, the data suggest that Basis 1X may improve liver function in healthy adults.

TABLE 4

Liver function Tests

| | Placebo Mean ± SD (n) | Basis 1X Mean ± SD (n) | Basis 2X Mean ± SD (n) | Between Group P Value |
|---|---|---|---|---|
| | | Bilirubin Concentration (µmol/L) | | |
| Day 0 Baseline | 11.6 ± 3.7 (40) | 11.2 ± 5.8 (40) | 11.3 ± 4.4 (40) | 0.697* § |
| Day 30 | 11.7 ± 4.8 (40) | 11.4 ± 6.4 (40) | 11.1 ± 3.9 (39) | 0.740* § |
| Day 60 End of Study | 11.4 ± 4.1 (40) | 10.5 ± 4.6 (40) | 11.6 ± 4.2 (37) | 0.344* § |
| Change from Day 0 to Day 30 | 0.14 ± 2.96 (40) | 0.19 ± 2.71 (40) | −0.45 ± 2.79 (39) | 0.641* Δ |
| Change from Day 0 to Day 60 | −0.1 ± 3.0 (40) | −0.7 ± 3.2 (40) | −0.2 ± 3.8 (37) | 0.635* Δ |
| | | Aspartate Transaminase (U/L) | | |
| Day 0 Baseline | 25.5 ± 6.3 (40) | 24.4 ± 9.5 (40) | 23.9 ± 5.9 (40) | 0.328 † |
| Day 30 | 26.1 ± 5.2 (40) | 23.8 ± 8.6 (40) | 25.1 ± 5.6 (39) | 0.004 † |
| Day 60 End of Study | 26.4 ± 6.1 (40) | 23.6 ± 8.7 (40) | 25.3 ± 5.7 (37) | 0.003 † |

TABLE 4-continued

Liver function Tests

|  | Placebo Mean ± SD (n) | Basis 1X Mean ± SD (n) | Basis 2X Mean ± SD (n) | Between Group P Value |
|---|---|---|---|---|
| Change from Day 0 to Day 30 | 0.6 ± 3.9 (40) | −0.6 ± 3.8 (40) | 1.1 ± 3.4 (39) | 0.047 † |
| Change from Day 0 to Day 60 | 0.8 ± 5.7 (40) | −0.8 ± 4.5 (40) | 0.9 ± 3.3 (37) | 0.041 † |
| Alanine Transaminase (U/L) | | | | |
| Day 0 Baseline | 23.4 ± 8.3 (40) | 21.6 ± 6.3 (40) | 21.9 ± 7.7 (40) | 0.584 † |
| Day 30 | 24.4 ± 9.3 (40) | 19.9 ± 5.4 (40) | 22.4 ± 7.2 (39) | 0.033 † |
| Day 60 End of Study | 25.1 ± 11.6 (40) | 19.7 ± 5.1 (40) | 21.8 ± 7.3 (37) | 0.039 † |
| Change from Day 0 to Day 30 | 1.0 ± 5.6 (40) | −1.7 ± 5.2 (40) [b] | 0.4 ± 5.1 (39) p = 0.267‡ | 0.032 † |
| Change from Day 0 to Day 60 | 1.6 ± 7.8 (40) | −1.9 ± 4.8 (40) [b] | −0.5 ± 5.0 (37) p = 0.968‡ | 0.127 † |
| Gamma-Glutamyltransferase (U/L) | | | | |
| Day 0 Baseline | 22 ± 13 (39) | 28 ± 56 (40) | 17 ± 11 (40) | 0.079 † |
| Day 30 | 24 ± 15 (40) | 28 ± 60 (40) | 18 ± 10 (39) | 0.092 † |
| Day 60 End of Study | 25 ± 18 (40) | 27 ± 56 (40) | 18 ± 11 (37) | 0.125 † |
| Change from Day 0 to Day 30 | 1.8 ± 6.5 (39) | −0.5 ± 9.2 (40) | 1.1 ± 4.0 (39) | 0.237 † |
| Change from Day 0 to Day 60 | 2.6 ± 6.9 (39) | −1.0 ± 8.8 (40) | 0.9 ± 6.4 (37) | 0.593 † |

Δ Between group comparisons were made using ANCOVA adjusting tor baseline.
† Between group comparisons were made using the non-parametric Kruskal-Wallis test
*The logarithmic transformation was required to achieve normality
[b] Within group comparisons were made using the paired Student t-test was significant p, 0.05.
Probability values P ≤ 0.05 are statistically significant.

Basis 1X and Blood Pressure

Vital signs, heart rate and blood pressure were measured in participants. There were no changes from baseline to Day 30 or 60 in heart rate or blood pressure in any group except in the Basis 1X group, where diastolic blood pressure decreased significantly at Day 60. See Table 5 below.

TABLE 5

Vital Signs of All Participants Randomized in the Study at Day 0, Day 30 and Day 60 (N = 120).

|  | Placebo Mean ± SD (n) | Basis 1X Mean ± SD (n) | Basis 2X Mean ± SD (n) | Between Group P Value Δ |
|---|---|---|---|---|
| Systolic Blood Pressure (mmHg) | | | | |
| Day 0 Baseline | 125.9 ± 14.2 (40) | 125.6 ± 15.9 (40) | 124.3 ± 16.0 (40) | 0.884 § |
| Day 30 | 123.9 ± 18.3 (40) | 125.9 ± 20.3 (40) | 124.3 ± 17.3 (38) | 0.877 § |
| Day 60 End of Study | 125.8 ± 13.4 (40) | 122.4 ± 19.2 (40) | 123.1 ± 15.6 (38) | 0.617 § |
| Change from Day 0 to Day 30 | −2.0 ± 13.5 (40) | 0.3 ± 12.8 (40) | −0.1 ± 12.2 (38) | 0.711 Δ |
| Change from Day 0 to Day 60 | −0.1 ± 10.7 (40) | −3.2 ± 14.0 (40) | −0.9 ± 11.1 (38) | 0.462 Δ |
| Diastolic Blood Pressure (mmHg) | | | | |
| Day 0 Baseline | 76.4 ± 10.5 (40) | 76.3 ± 9.8 (40) | 75.2 ± 8.0 (40) | 0.815 § |
| Day 30 | 75.6 ± 10.8 (40) | 75.5 ± 12.2 (40) | 75.5 ± 9.1 (38) | 0.998 § |
| Day 60 End of Study | 76.1 ± 10.1 (40) | 72.9 ± 10.1 (40) | 75.0 ± 9.2 (38) | 0.346 § |
| Change from Day 0 to Day 30 | −0.8 ± 7.4 (40) | −0.7 ± 9.1 (40) | 0.6 ± 7.4 (38) | 0.804 Δ |
| Change from Day 0 to Day 60 | −0.3 ± 8.2 (40) | −3.4 ± 7.1 (40)[b] | −0.1 ± 7.0 (38) | 0.092 Δ |

TABLE 5-continued

Vital Signs of All Participants Randomized in the Study at Day 0, Day 30 and Day 60 (N = 120).

|  | Placebo Mean ± SD (n) | Basis 1X Mean ± SD (n) | Basis 2X Mean ± SD (n) | Between Group P Value Δ |
|---|---|---|---|---|
| Heart Rate (BPM) | | | | |
| Day 0 Baseline | 65.6 ± 8.0 (40) | 70.3 ± 10.9 (40) | 67.3 ± 10.5 (40) | 0.104 § |
| Day 30 | 66.7 ± 9.2 (40) | 68.5 ± 10.2 (40) | 66.1 ± 9.2 (38) | 0.532 § |
| Day 60 End of Study | 67.6 ± 10.0 (40) | 68.7 ± 9.6 (40) | 64.9 ± 8.3 (38) | 0.186 § |
| Change from Day 0 to Day 30 | 1.1 ± 6.8 (40) | −1.9 ± 8.1 (40) | −0.0 ± 8.9 (38) | 0.708 Δ |
| Change from Day 0 to Day 60 | 2.0 ± 7.6 (40) | −1.7 ± 8.0 (40) | −1.5 ± 8.1 (38) | 0.146 Δ |

BPM, beats per minute; kg, kilograms; Max, maximum; mmHg, m, meter; mmHg, millimeters of mercury; Min, minimum; N, number; SD, standard deviation.
§ Between group comparisons were made using ANOVA.
Δ Between group comparisons were made using ANCOVA adjusting for baseline.
[b]Within group comparisons were made using the paired Student t-test were significant p, 0.05.
Probability values $P \leq 0.05$ are statistically significant.

Basis and Other Blood Markers

Hematology and Clinical Chemistry Parameters in Participants after a 60-day Supplementation with Basis 1X, Basis 2X or placebo showed no significant differences between Basis 1X, Basis 2X or placebo in hemoglobin, hematocrit, WBC, RBC, mean corpuscular volume, mean corpuscular hemoglobin, counts of platelet, neutrophil, lymphocytes, monocytes, eosinophils, basophils. Electrolytes (sodium, potassium, and chloride) concentration and kidney function as measured by creatinine were similar between groups throughout the study (Table 6).

TABLE 6

Haematology and Clinical Chemistry Parameters of All Randomized Participants at Baseline (Day 0), and Day 30, and Day 60 (N = 120)

|  | Placebo Mean ± SD (n) | Basis 1X Mean ± SD (n) | Basis 2X Mean ± SD (n) | Between Group P Value |
|---|---|---|---|---|
| Hemoglobin Concentration (g/L) | | | | |
| Day 0 Baseline | 140.4 ± 14.4 (40) | 136.8 ± 11.7 (40) | 140.4 ± 13.5 (40) | 0.382 § |
| Day 30 | 139.6 ± 12.6 (39) | 136.5 ± 11.2 (40)) | 139.6 ± 11.4 (38) | 0.401 § |
| Day 60 End of Study | 138.8 ± 13.1 (40) | 135.5 ± 11.7 (40) | 139.8 ± 11.2 (37) | 0.268 § |
| Change from Day 0 to Day 30 | −1.2 ± 6.0 (39) | −0.3 ± 4.8 (40) | −0.2 ± 4.2 (38) | 0.685 Δ |
| Change from Day 0 to Day 60 | −1.6 ± 6.0 (40) | −1.4 ± 5.1 (40) | −0.4 ± 4.9 (37) | 0.417 Δ |
| Hematocrit (L/L) | | | | |
| Day 0 Baseline | 0.414 ± 0.040 (40) | 0.406 ± 0.032 (40) | 0.417 ± 0.037 (40) | 0.392 § |
| Day 30 | 0.413 ± 0.035 (39) | 0.405 ± 0.029 (40) | 0.414 ± 0.029 (38) | 0.372 § |
| Day 60 End of Study | 0.410 ± 0.037 (40) | 0.405 ± 0.029 (40) | 0.412 ± 0.029 (37) | 0.593 § |
| Change from Day 0 to Day 30 | −0.0019 ± 0.0168 (39) | −0.0008 ± 0.0141 (40) | −0.0004 ± 0.0116 (38) | 0.780 Δ |
| Change from Day 0 to Day 60 | −0.0039 ± 0.0165 (40) | −0.0013 ± 0.0150 (40) | −0.0038 ± 0.0119 (37) | 0.917 Δ |
| White Blood Cell Count (x E9/L) | | | | |
| Day 0 Baseline | 5.70 ± 1.68 (40) | 6.02 ± 1.81 (40) | 5.88 ± 2.26 (40) | 0.794* § |
| Day 30 | 5.48 ± 1.55 (39) | 5.91 ± 1.54 (40) | 5.30 ± 1.31 (38) | 0.241* § |
| Day 60 End of Study | 5.63 ± 1.83 (40) | 5.76 ± 1.41 (40) | 5.33 ± 1.48 (37) | 0.442* § |

TABLE 6-continued

Haematology and Clinical Chemistry Parameters of All Randomized Participants
at Baseline (Day 0), and Day 30, and Day 60 (N = 120)

|  | Placebo<br>Mean ± SD (n) | Basis 1X<br>Mean ± SD (n) | Basis 2X<br>Mean ± SD (n) | Between<br>Group<br>P Value |
|---|---|---|---|---|
| Change from Day 0 to Day 30 | −0.23 ± 0.90 (39) | −0.11 ± 1.65 (40) | −0.57 ± 1.93 (38) | 0.176* Δ |
| Change from Day 0 to Day 60 | −0.06 ± 0.96 (40) | −0.26 ± 1.15 (40) | −0.51 ± 2.02 (37) | 0.319* Δ |
| Red Blood Cell Count (x E12/L) | | | | |
| Day 0 Baseline | 4.58 ± 0.46 (40) | 4.56 ± 0.36 (40) | 4.63 ± 0.44 (40) | 0.757* § |
| Day 30 | 4.57 ± 0.41 (39) | 4.54 ± 0.35 (40) | 4.61 ± 0.37 (38) | 0.745* § |
| Day 60 End of Study | 4.55 ± 0.42 (40) | 4.55 ± 0.38 (40) | 4.60 ± 0.39 (37) | 0.779* § |
| Change from Day 0 to Day 30 | −0.025 ± 0.185 (39) | −0.019 ± 0.127 (40) | −0.001 ± 0.119 (38) | 0.619* Δ |
| Change from Day 0 to Day 60 | −0.033 ± 0.182 (40) | −0.008 ± 0.152 (40) | −0.009 ± 0.142 (37) | 0.738* Δ |
| Mean Corpuscular Volume (fL) | | | | |
| Day 0 Baseline | 90.3 ± 3.5 (40) | 89.1 ± 3.2 (40) | 90.0 ± 4.5 (40) | 0.318* § |
| Day 30 | 90.4 ± 3.2 (39) | 89.4 ± 3.3 (40) | 90.1 ± 4.4 (38) | 0.453* § |
| Day 60 End of Study | 90.2 ± 3.3 (40) | 89.1 ± 3.5 (40) | 89.6 ± 4.4 (37) | 0.409* § |
| Change from Day 0 to Day 30 | 0.18 ± 1.07 (39) | 0.30 ± 1.92 (40) | 0.05 ± 1.21 (38) | 0.879* Δ |
| Change from Day 0 to Day 60 | −0.15 ± 1.08 (40) | −0.02 ± 1.89 (40) | −0.54 ± 1.30 (37) | 0.338* Δ |
| Mean Corpuscular Hemoglobin (pg) | | | | |
| Day 0 Baseline | 30.74 ± 1.48 (40) | 30.02 ± 1.29 (40) | 30.34 ± 1.60 (40) | 0.099* § |
| Day 30 | 30.54 ± 1.30 (39) | 30.08 ± 1.40 (40) | 30.36 ± 1.74 (38) | 0.376* § |
| Day 60 End of Study | 30.53 ± 1.31 (40) | 29.80 ± 1.40 (40) | 30.42 ± 1.76 (37) | 0.071* § |
| Change from Day 0 to Day 30 | −0.16 ± 0.73 (39) | 0.06 ± 0.84 (40) | −0.01 ± 0.44 (38) | 0.634* Δ |
| Change from Day 0 to Day 60 | −0.21 ± 0.70 (40) | −0.22 ± 0.75 (40) | −0.00 ± 0.58 (37) | 0.274* Δ |
| Mean Corpuscular Hemoglobin Concentration (g/L) | | | | |
| Day 0 Baseline | 339.6 ± 6.8 (40) | 337.0 ± 6.1 (40) | 337.4 ± 7.0 (40) | 0.183 § |
| Day 30 | 338.1 ± 7.1 (39) | 336.8 ± 6.6 (40) | 336.9 ± 7.1 (38) | 0.643 § |
| Day 60 End of Study | 338.8 ± 7.0 (40) | 334.8 ± 7.1 (40) | 339.2 ± 6.2 (37) | 0.007 § |
| Change from Day 0 to Day 30 | −1.6 ± 4.9 (39) | −0.2 ± 6.3 (40) | −0.7 ± 4.8 (38) | 0.898 Δ |
| Change from Day 0 to Day 60 | −0.8 ± 5.2 (40) | −2.3 ± 4.4 (40) | 1.4 ± 6.5 (37) | 0.003 Δ |
| Red Cell Distribution Width (%) | | | | |
| Day 0 Baseline | 13.63 ± 0.56 (40) | 14.00 ± 0.68 (40)[a] | 13.66 ± 0.46 (40) | 0.008* § |
| Day 30 | 13.55 ± 0.54 (39) | 13.98 ± 0.63 (40) | 13.69 ± 0.48 (38) | 0.002* § |
| Day 60 End of Study | 13.53 ± 0.58 (40) | 13.91 ± 0.63 (40) | 13.66 ± 0.45 (37) | 0.011* § |
| Change from Day 0 to Day 30 | −0.062 ± 0.298 (39) | −0.015 ± 0.280 (40) | 0.021 ± 0.204 (38) | 0.150* Δ |
| Change from Day 0 to Day 60 | −0.10 ± 0.37 (40) | −0.08 ± 0.41 (40) | −0.02 ± 0.27 (37) | 0.388* Δ |

TABLE 6-continued

Haematology and Clinical Chemistry Parameters of All Randomized Participants at Baseline (Day 0), and Day 30, and Day 60 (N = 120)

| | Placebo Mean ± SD (n) | Basis 1X Mean ± SD (n) | Basis 2X Mean ± SD (n) | Between Group P Value |
|---|---|---|---|---|
| Platelet Count (x E9/L) | | | | |
| Day 0 Baseline | 251 ± 47 (40) | 244 ± 51 (39) | 252 ± 57 (40) | 0.758* § |
| Day 30 | 250 ± 48 (39) | 246 ± 51 (40) | 251 ± 59 (38) | 0.933* § |
| Day 60 End of Study | 250 ± 49 (40) | 253 ± 54 (39) | 250 ± 60 (37) | 0.942* § |
| Change from Day 0 to Day 30 | 0.2 ± 20.3 (39) | 2.5 ± 24.5 (39) | −0.6 ± 25.7 (38) | 0.850* Δ |
| Change from Day 0 to Day 60 | −0.8 ± 21.6 (40) | 8.9 ± 28.4 (38) | −1.2 ± 25.4 (37) | 0.134* Δ |
| Neutrophil Count (x E9/L) | | | | |
| Day 0 Baseline | 3.18 ± 1.23 (40) | 3.46 ± 1.43 (40) | 3.17 ± 1.04 (40) | 0.738* § |
| Day 30 | 3.05 ± 1.15 (39) | 3.19 ± 0.99 (40) | 2.85 ± 0.96 (38) | 0.384* § |
| Day 60 End of Study | 3.18 ± 1.44 (40) | 3.22 ± 0.95 (40) | 2.88 ± 1.12 (37) | 0.293* § |
| Change from Day 0 to Day 30 | −0.15 ± 0.77 (39) | −0.27 ± 1.17 (40) | −0.32 ± 0.71 (38) | 0.377* Δ |
| Change from Day 0 to Day 60 | 0.00 ± 0.79 (40) | −0.24 ± 1.02 (40) | −0.25 ± 0.95 (37) | 0.282* Δ |
| Lymphocyte Count (x E9/L) | | | | |
| Day 0 Baseline | 1.80 ± 0.57 (40) | 1.83 ± 0.64 (40) | 1.76 ± 0.43 (40) | 0.962* § |
| Day 30 | 1.71 ± 0.48 (39) | 1.88 ± 0.68 (40) | 1.78 ± 0.48 (38) | 0.628* § |
| Day 60 End of Study | 1.75 ± 0.49 (40) | 1.84 ± 0.59 (40) | 1.76 ± 0.45 (37) | 0.771* § |
| Change from Day 0 to Day 30 | −0.082 ± 0.266 (39) | 0.045 ± 0.292 (40) | 0.032 ± 0.266 (38) | 0.264* Δ |
| Change from Day 0 to Day 60 | −0.045 ± 0.343 (40) | 0.012 ± 0.236 (40) | 0.016 ± 0.285 (37) | 0.639* Δ |
| Monocyte Count (x E9/L) | | | | |
| Day 0 Baseline | 0.497 ± 0.151 (40) | 0.503 ± 0.191 (40) | 0.473 ± 0.157 (40) | 0.682 † |
| Day 30 | 0.485 ± 0.137 (39) | 0.477 ± 0.191 (40) | 0.458 ± 0.120 (38) | 0.785 † |
| Day 60 End of Study | 0.497 ± 0.202 (40) | 0.500 ± 0.178 (40) | 0.465 ± 0.148 (37) | 0.729 † |
| Change from Day 0 to Day 30 | −0.013 ± 0.092 (39) | −0.025 ± 0.150 (40) | −0.011 ± 0.095 (38) | 0.879 † |
| Change from Day 0 to Day 60 | 0.000 ± 0.118 (40) | −0.002 ± 0.140 (40) | −0.014 ± 0.111 (37) | 0.701 † |
| Eosinophil Count (x E9/L) | | | | |
| Day 0 Baseline | 0.182 ± 0.108 (40) | 0.178 ± 0.103 (40) | 0.182 ± 0.103 (40) | 0.901 † |
| Day 30 | 0.179 ± 0.149 (39) | 0.198 ± 0.125 (40) | 0.192 ± 0.115 (38) | 0.374 † |
| Day 60 End of Study | 0.180 ± 0.094 (40) | 0.195 ± 0.106 (40) | 0.189 ± 0.110 (37) | 0.810 † |
| Change from Day 0 to Day 30 | −0.005 ± 0.102 (39) | 0.020 ± 0.091 (40) | 0.008 ± 0.063 (38) | 0.110 † |
| Change from Day 0 to Day 60 | −0.002 ± 0.092 (40) | 0.017 ± 0.081 (40) | 0.005 ± 0.066 (37) | 0.763 † |
| Basophil Count (x E9/L) | | | | |
| Day 0 Baseline | 0.020 ± 0.041 (40) | 0.025 ± 0.044 (40) | 0.018 ± 0.038 (40) | 0.704 † |
| Day 30 | 0.028 ± 0.046 (39) | 0.022 ± 0.042 (40) | 0.021 ± 0.041 (38) | 0.739 † |
| Day 60 End of Study | 0.025 ± 0.044 (40) 0 (0-0.1) | 0.020 ± 0.041 (40) 0 (0-0.1) | 0.022 ± 0.042 (37) | 0.862 † |

TABLE 6-continued

Haematology and Clinical Chemistry Parameters of All Randomized Participants at Baseline (Day 0), and Day 30, and Day 60 (N = 120)

|  | Placebo<br>Mean ± SD (n) | Basis 1X<br>Mean ± SD (n) | Basis 2X<br>Mean ± SD (n) | Between<br>Group<br>P Value |
|---|---|---|---|---|
| Change from Day 0 to Day 30 | 0.008 ± 0.042 (39) | −0.002 ± 0.036 (40) | 0.003 ± 0.028 (38) | 0.447 † |
| Change from Day 0 to Day 60 | 0.005 ± 0.045 (40) | −0.005 ± 0.032 (40) | 0.003 ± 0.037 (37) | 0.472 † |
| Creatinine Concentration (μmol/L) | | | | |
| Day 0 Baseline | 71.3 ± 12.5 (40) | 69.4 ± 16.0 (40) | 69.2 ± 16.0 (40) | 0.624* § |
| Day 30 | 70.9 ± 11.6 (40) | 66.7 ± 14.1 (40) | 68.6 ± 17.2 (39) | 0.269* § |
| Day 60 End of Study | 70.1 ± 11.2 (40) | 68.0 ± 15.5 (40) | 67.0 ± 15.1 (37) | 0.421* § |
| Change from Day 0 to Day 30 | −0.5 ± 6.5 (40) | −2.8 ± 7.8 (40) | −0.9 ± 5.7 (39) | 0.181*Δ |
| Change from Day 0 to Day 60 | −1.3 ± 6.1 (40) | −1.5 ± 7.7 (40) | −2.9 ± 4.9 (37) | 0.353* Δ |
| Sodium Concentration (mmol/L) | | | | |
| Day 0 Baseline | 140.75 ± 2.59 (40) | 141.45 ± 1.47 (40) | 141.12 ± 1.86 (40) | 0.306 § |
| Day 30 | 140.40 ± 2.57 (40) | 141.32 ± 1.89 (40) | 141.51 ± 2.14 (39) | 0.061 § |
| Day 60 End of Study | 141.05 ± 3.00 (40) | 141.60 ± 1.89 (40) | 140.97 ± 2.02 (37) | 0.442 § |
| Change from Day 0 to Day 30 | −0.35 ± 1.86 (40) | −0.12 ± 2.05 (40) | 0.36 ± 1.83 (39) | 0.113 Δ |
| Change from Day 0 to Day 60 | 0.30 ± 3.00 (40) | 0.15 ± 2.01 (40) | −0.19 ± 2.07 (37) | 0.612 Δ |
| Potassium Concentration (mmol/L) | | | | |
| Day 0 Baseline | 4.44 ± 0.38 (40) | 4.39 ± 0.32 (40) | 4.34 ± 0.34 (40) | 0.506* § |
| Day 30 | 4.42 ± 0.41 (40) | 4.33 ± 0.33 (40) | 4.32 ± 0.37 (39) | 0.413* § |
| Day 60 End of Study | 4.36 ± 0.43 (40) | 4.38 ± 0.27 (40) | 4.29 ± 0.25 (37) | 0.411* § |
| Change from Day 0 to Day 30 | −0.02 ± 0.43 (40) | −0.06 ± 0.40 (40) | −0.03 ± 0.35 (39) | 0.588* Δ |
| Change from Day 0 to Day 60 | −0.08 ± 0.42 (40) | −0.00 ± 0.38 (40) | −0.07 ± 0.37 (37) | 0.453* Δ |
| Chloride Concentration (mmol/L) | | | | |
| Day 0 Baseline | 104.8 ± 3.8 (40) | 105.5 ± 2.5 (40) | 105.2 ± 3.3 (40) | 0.931 † |
| Day 30 | 104.9 ± 3.4 (40) | 105.6 ± 3.0 (40) | 106.1 ± 2.6 (39) | 0.344 † |
| Day 60 End of Study | 105.0 ± 3.7 (40) | 105.6 ± 2.8 (40) | 106.0 ± 2.6 (37) | 0.497 † |
| Change from Day 0 to Day 30 | 0.10 ± 2.26 (40) | 0.07 ± 1.79 (40) | 0.62 ± 2.50 (39) | 0.533 † |
| Change from Day 0 to Day 60 | 0.25 ± 2.88 (40) | 0.07 ± 1.82 (40) | 0.62 ± 1.74 (37) | 0.527 † |

Incorporation by Reference

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating or preventing fatty liver in a subject comprising administering to the subject a composition comprising nicotinamide riboside and pterostilbene, wherein the composition is administered to the subject once daily, and the once daily dose of the composition comprises 250 mg of nicotinamide riboside and 50 mg pterostilbene.

2. The method of claim 1, wherein the composition is administered for at least 2 months.

3. The method of claim 1, wherein the composition is administered for at least 6 months.

4. The method of claim 1, wherein the composition is formulated as a pill, a tablet, or a capsule.

5. The method of claim 1, wherein the composition is administered orally.

6. The method of claim 1, wherein the composition is self-administered.

7. The method of claim 1, wherein the subject has elevated serum levels of aspartate transaminase (AST) or alanine transaminase (ALT).

8. The method of claim 1, wherein the subject has non-alcoholic fatty liver disease.

* * * * *